United States Patent
Hui

(10) Patent No.: US 11,460,917 B2
(45) Date of Patent: Oct. 4, 2022

(54) CONTROL METHOD AND CONTROL APPARATUS OF DISPLAY UNIT IN MEDICAL SYSTEM

(71) Applicant: GE Precision Healthcare LLC, Wauwatosa, WI (US)

(72) Inventor: Hui Hui, WuXi (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 5 days.

(21) Appl. No.: 17/118,826

(22) Filed: Dec. 11, 2020

(65) Prior Publication Data

US 2021/0200306 A1 Jul. 1, 2021

(30) Foreign Application Priority Data

Dec. 27, 2019 (CN) .......................... 201911378048.5

(51) Int. Cl.
*G06F 3/01* (2006.01)
*A61B 5/00* (2006.01)
*G16H 40/63* (2018.01)
*G06V 40/16* (2022.01)
*G06V 40/18* (2022.01)

(52) U.S. Cl.
CPC .............. *G06F 3/013* (2013.01); *A61B 5/742* (2013.01); *G06V 40/168* (2022.01); *G06V 40/172* (2022.01); *G06V 40/193* (2022.01); *G16H 40/63* (2018.01)

(58) Field of Classification Search
CPC ..... G06F 3/013; G06F 3/04847; A61B 5/742; A61B 5/1079; A61B 5/1176; A61B 5/1171; G06V 40/168; G06V 40/172; G06V 40/193; G06V 40/18; G06V 40/16; G16H 40/63; G16H 30/40; G16H 50/20
See application file for complete search history.

(56) References Cited

U.S. PATENT DOCUMENTS

2006/0109237 A1* 5/2006 Morita ................... G16H 40/63
345/156
2012/0075166 A1* 3/2012 Marti .................. G02B 27/0093
345/1.1

* cited by examiner

*Primary Examiner* — Abhishek Sarma

(57) ABSTRACT

A control method of a display unit in a medical system, the control method including: acquiring an environmental image of the display unit; acquiring, according to the environmental image, feature information of at least one user therein; and determining a specific user of the at least one user according to the feature information so as to generate a control signal, the control signal being used to drive the display unit to rotate such that the specific user watches the display unit easily. The present invention also provides a control apparatus of a display unit in a medical system to implement the method.

12 Claims, 5 Drawing Sheets

CONTROL METHOD AND CONTROL APPARATUS OF DISPLAY UNIT IN MEDICAL SYSTEM

TECHNICAL FIELD

This application claims the benefit of Chinese Patent Application No. 201911378048.5 filed on Dec. 27, 2019, the disclosure of which is herein incorporated by reference in its entirety.

The present invention relates to the medical field, and in particular relates to a medical system and a control method and a control apparatus of a display unit in the medical system, and a non-transitory computer-readable storage medium.

BACKGROUND

Common medical systems include imaging systems such as an ultrasound imaging system, a magnetic resonance imaging system, an X-ray imaging system, and the like, and other medical systems such as a monitoring system, an electrocardiogram system, an anaesthetic system, and the like. Users can use these medical systems to rapidly and accurately acquire related information about an examinee, so as to provide a corresponding suggestion or tactic regarding a health status or other physical parameters of the examinee.

With the continuous development of the medical systems, the human-machine interaction between users and the medical systems becomes more and more frequent. A display unit as part of a medical system is an important component for implementing human-machine interaction. The display unit allows various information acquired by the medical system to be rapidly transmitted to users in real time. A user can also use the display unit to acquire various parameter information required thereby, and determine whether an operation performed thereby on the medical system is accurate.

In some application scenarios, multiple potential users may be present in the same environment, and these potential users may have different degrees of watching requirements with respect to the display unit. However, it is difficult for the display unit to determine the degrees of watching requirements of the users, such that a specific user may not be able to watch the display unit.

SUMMARY

In some embodiments of the present invention, a control method of a display unit in a medical system is provided, the control method comprising: acquiring an environmental image of the display unit; acquiring, according to the environmental image, feature information of at least one user therein; and determining a specific user of the at least one user according to the feature information so as to generate a control signal, the control signal being used to drive the display unit to rotate such that the specific user watches the display unit easily.

Optionally, the feature information comprises facial information or eye information of the user.

Optionally, the control signal comprises a signal for driving the display unit to rotate by a certain angle.

Optionally, determining a specific user of the at least one user according to the feature information so as to generate a control signal comprises: identifying the user according to the feature information, comparing the identified user with preset information, and determining the specific user of the at least one user according to a comparison result so as to generate a corresponding control signal.

Optionally, the preset information comprises priority information of different users; comparing the identified user with preset information comprises: comparing the identified user with the priority information, and determining a priority level of the user.

Optionally, the control signal is configured to: drive the display unit to rotate by a certain angle towards the specific user having a high priority level.

Optionally, the feature information comprises first feature information and second feature information corresponding to the first feature information.

Optionally, the first feature information comprises the eye information of the user; the second feature information comprises the facial information of the user.

Optionally, determining a specific user of the at least one user according to the feature information so as to generate a control signal comprises: determining a watching requirement of the user with respect to the display unit according to the first feature information; identifying the user according to the second feature information, and comparing the user with preset information; and determining the specific user of the at least one user according to a determination result of the watching requirement and a result of the comparison so as to generate the corresponding control signal.

Optionally, the preset information comprises priority information of different users; comparing the user with preset information further comprises: comparing the user with the priority information, and determining a priority level of the user.

Optionally, the control signal is configured to: drive the display unit to rotate by a certain angle towards the specific user having a high priority level and having the watching requirement.

In some other embodiments of the present invention, a control apparatus of a display unit in a medical system is provided, the control apparatus comprising: an environmental image generation unit; a processing unit; and a drive unit, wherein the environmental image generation unit is used to generate an environmental image and transmit the environmental image to the processing unit; the processing unit is used to perform the method described above so as to transmit a control signal to the drive unit; and the drive unit is used to receive the control signal so as to drive the display unit to rotate.

In some other embodiments of the present invention, a medical system is provided, the medical system comprising the above described control apparatus.

In some other embodiments of the present invention, a non-transitory computer-readable storage medium is provided, the non-transitory computer-readable storage medium storing a computer program, wherein when executed by a computer, the computer program causes the computer to perform the above described control method.

It should be understood that the brief description above is provided to introduce in simplified form some concepts that will be further described in the Detailed Description of the Embodiments. The brief description above is not meant to identify key or essential features of the claimed subject matter. The scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

The present invention may be better understood by describing exemplary embodiments of the present invention with reference to accompanying drawings, in which.

DETAILED DESCRIPTION OF THE EMBODIMENTS

The embodiments of the present invention will be described in detail hereinbelow. It should be noted that during the process of describing the embodiments in detail, it is impossible to describe all features of the actual embodiments in detail in this description for the sake of brevity. It should be understood that in the actual implementation of any of the embodiments, as in the process of any engineering project or design project, a variety of specific decisions are often made in order to achieve the developer's specific objectives and meet system-related or business-related restrictions, and the decisions vary from one embodiment to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The words "first," "second" and similar words used in the description and claims of the patent application of the present invention do not denote any order, quantity or importance, but are merely intended to distinguish between different constituents. "One," "a(n)" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

Figure 1:
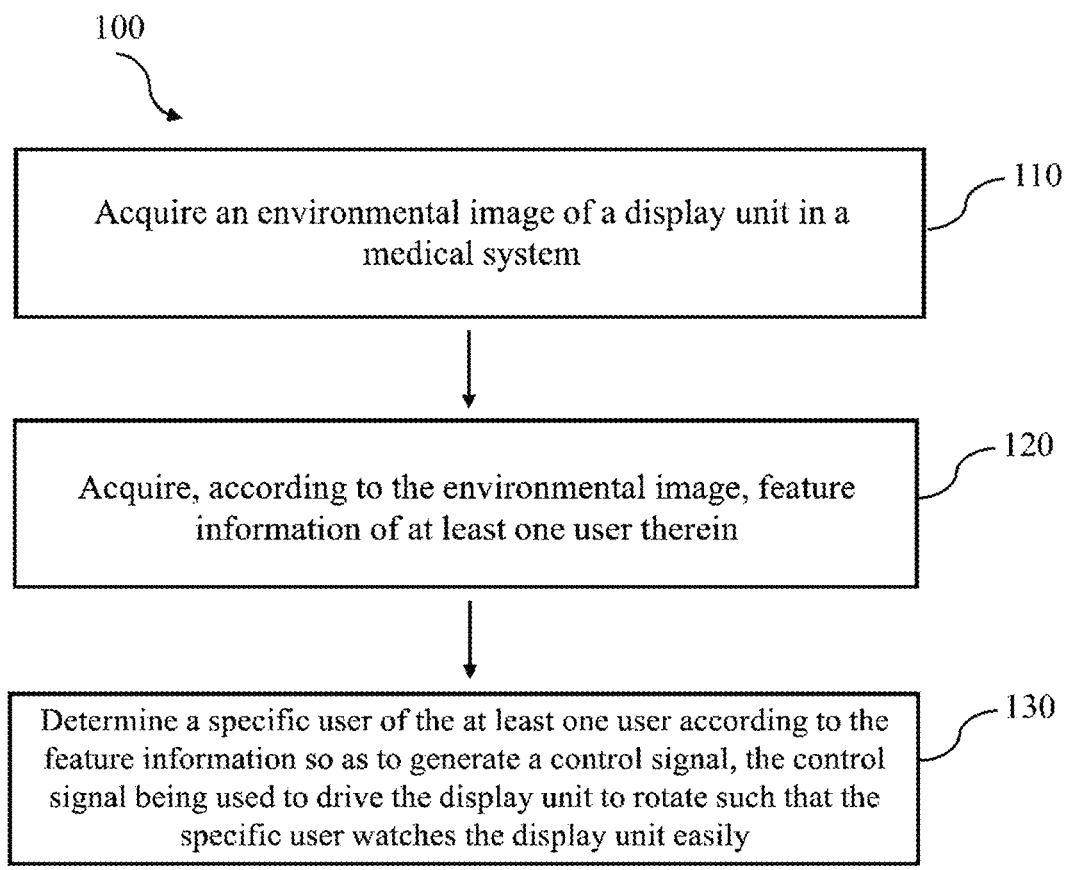
FIG. 1 shows a schematic diagram of a control method of a display unit in a medical system according to some embodiments of the present invention.

Referring to FIG. 1 first, FIG. 1 shows a control method 100 of a display unit in a medical system according to some embodiments of the present invention. The above described medical systems can include, but are not limited to, medical systems such as an ultrasound imaging system, a magnetic resonance imaging system, an X-ray imaging system, a monitoring system, an electrocardiogram system, an anaesthetic system, and the like. In some embodiments of this specification, a monitoring system is used as an example for description. The monitoring system has a variety of application scenarios, such as a ward, an emergency room, an operating room, and the like. A display unit of an existing monitoring system is usually placed with a preset certain angle or fixedly disposed in a certain position. Once configuration is completed, the orientation of the display unit cannot be easily adjusted. In some operating environments, a user (such as a doctor, a nurse, or a patient) may need to walk around, and may have a watching requirement on the above described display unit from time to time. However, when the user walks to certain positions, it may be difficult for the user to watch the display unit. In addition, multiple potential users may be present in the same environment, and these potential users may have different degrees of watching requirements with respect to the display unit. However, it is difficult for the display unit to determine the degrees of watching requirements of the users, such that a specific user may not be able to watch the display unit.

In order to solve at least part of the above described problems, the control method 100 of some embodiments of the present invention includes the following steps:

Step S110, acquire an environmental image of the above described display unit. The environmental image can be an image of an external environment in which the display unit is located, and the external environment includes, but is not limited to, a ward, an emergency room, an operating room, an examination room, or any other scenario in which the medical system may be used. In some embodiments, the environmental image can be acquired in real time, and for example, real-time image acquisition is performed by using an imaging tool such as a camera, a video camera, and the like. In addition, the above described environmental image can also be acquired and stored in advance by using a tool such as a memory, such that the environmental image can be acquired by accessing the memory. It should be noted that during real-time image acquisition, the imaging tool such as a camera, a video camera, and the like can be separately disposed independent of the display unit, and can also be integrated on the display unit. In certain cases, an imaging range covered by the imaging tool is limited. For example, image information at the back of the imaging tool cannot be acquired. In some embodiments of the present invention, multiple imaging tools are provided, and imaging ranges of the multiple imaging tools are appropriately arranged, such that the entire external environment can be covered to perform image acquisition.

Step S120, acquire, according to the environmental image, feature information of at least one user therein. Information included in the environmental image acquired in step S110 may be varied, and may include, for example, information about a user, a wall, a hospital bed, and the like. In step S120, acquire feature information of at least one user included in the above described environmental image. The above described feature information can be varied. For example, the feature information is a body contour or a head contour of the user, or any limb, any organ, or the like that can distinguish the user from other objects in the environmental image. It should be noted that the above described user is not necessarily a user (such as a doctor or a nurse) operating the display unit or the medical system, and may be a user (such as a patient or an examinee) having a potential watching requirement with respect to the display unit. However, in certain embodiments, it can also be specified that the above described user refers only to a professional such as a doctor or a nurse who actually uses the display unit or the medical system. In some embodiments, the above described feature information can be face information. Correspondingly, identification of the feature information can be performed by using face recognition technology in the prior art. In some other embodiments, the above described feature information can further be eye information. Correspondingly, identification of the feature information can be performed by using eye recognition technology in the prior art. In some other embodiments, the above described feature information can further be clothing information or the like of the user. For example, the above described feature information is information such as a mask or a hat worn by the user. The advantage of such configurations is that medical staff can be accurately identified according to the above described clothing information, such that in the succeeding step, adjustment of the display unit benefits the medical staff.

Step S130, determine a specific user of the at least one user according to the feature information so as to generate a control signal, the control signal being used to drive the display unit to rotate such that the specific user watches the display unit easily. Identification is performed on the feature information of the at least one user in step S120, and the identification can distinguish the user from the other objects in the environmental image. The specific user can be any one or more users among identified users. The specific user can also be a user located relatively in the center among all of the identified users. Alternatively, the specific user can also be a medical staff member having a higher watching requirement with respect to the display unit or the medical system, and in this case, determination can be performed according to clothing information and the like. On this basis, the control signal is generated. The control signal can be configured to drive the display unit to rotate, such that the specific user can easily watch the display unit. It should be noted that rotation can be varied. For example, rotation is performed horizontally first, and is then performed vertically; or, the display unit is turned arbitrarily, which is also regarded as rotation.

In some embodiments, the control signal can include a signal for driving the display unit to rotate by a certain angle. The control signal can be configured by using the following method: the feature information, such as the body contour, the head contour, the face information, or the like, of the user is identified, so as to determine a feature information point such as a central point of the body contour, the head contour, or the face. Then, a connecting line between the central point and a central point of the display unit is determined. Further, an included angle formed by the connecting line and a perpendicular bisector of the display unit can be determined. The control signal can be configured according to the included angle, so as to cause the display unit to rotate in a direction to reduce or even eliminate the included angle. Configuration of the control signal can be varied. In some embodiments, a fixed rotation angle, such as 5° to 20°, can be preset. After rotation is performed once, the aforementioned steps are performed again to determine whether the above described included angle has been reduced to be less than a certain threshold. If so, rotation can be stopped; if not, a control signal can be transmitted again to control the display unit to rotate until the above described included angle is less than the threshold. In some embodiments, the above described certain angle can be consistent with the above described included angle. For example, when the measured included angle is 30°, a control signal of rotating by 30° is correspondingly transmitted to eliminate the included angle. In this way, the control signal is transmitted only once to achieve a technical effect of allowing the specific user to watch easily. In certain scenarios, the specific user may be moving, and the environmental image can be acquired at certain time intervals, such as at an interval of 5-10 seconds, or at other time intervals, such that the specific user can watch easily in dynamic scenarios. It should be noted that the above described control signal is some preferred embodiments of the present invention, and other existing control methods are also applicable.

Figure 2:
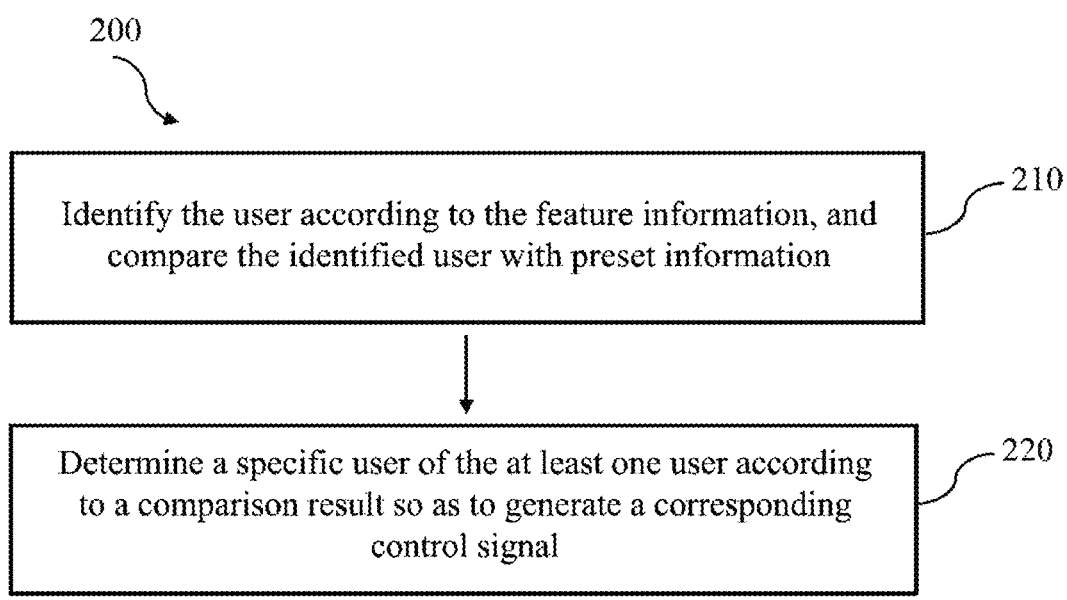
FIG. 2 shows a schematic diagram of a control signal generation method according to some embodiments of the present invention.

Referring to FIG. 2, FIG. 2 shows a schematic method diagram 200 of generating a control signal according to feature information according to some embodiments of the present invention. In some embodiments, the method of the present invention can include configuring preset information. The above described preset information can be acquired and stored in advance by using a tool such as a memory, such that the preset information can be acquired by accessing the memory. When the control signal is generated according to the above described feature information, the feature information acquired by means of identification can be compared with the preset information, and the corresponding control signal is generated according to a comparison result.

In step S210, identify a user according to feature information, and compare the identified user with preset information. Configuration of the above described preset information can be varied. In some embodiments, the preset information can be priority information of different users. For example, feature information of multiple users which may use a display unit or a medical system is acquired in advance. Then, the users corresponding to the above described feature information are sorted according to certain priorities. That is, priority information of different users is configured. Rules for configuration can be varied. In some embodiments, sorting can be performed according to levels of importance of the users. For example, sorting can be performed according to degrees of criticality of medical staff in an operating room, or degrees of importance of nurses in a ward, or the like. In some embodiments, the above described feature information can be face information. Correspondingly, during storage of the priority information, face information of users such as medical staff and the like can be acquired easily in advance by means of face recognition technology and the like, and presetting can be performed according to a priority rule. It should be noted that as described above, the feature information can be of other types, such as eye information, clothing information, and the like. During presetting, the corresponding priority information, such as the eye information, the clothing information, and the like, can be preset according to the method of the present invention.

After feature information of at least one user in an environmental image is identified, correspondingly the user corresponding to the above described feature information can be compared with preset user priority information, so as to determine a priority level of the above described user. In some embodiments, multiple users may be present. In step S220, determine a specific user of the at least one user according to a comparison result so as to generate a corresponding control signal. The corresponding control signal can be generated by determining the priority level of the above described feature information, so as to determine one or a plurality of the multiple users to whom the display unit should rotate to. For example, the control signal can be configured to drive the display unit to rotate by a certain angle towards a user corresponding to feature information having a high priority level. Regarding determination of the rotation angle, reference can be made to some embodiments described above, and other methods in the prior art can also be used. Details will not be described herein again.

The priority level of the user is determined, and the corresponding control signal is generated, thereby ensuring that in some application scenarios a specific user can easily watch the above described display unit and medical system. Especially in some scenarios in which a relatively large number of users are present, the priority is determined, such that the display unit is preferentially directed to a user having a high priority level, and interference from other unnecessary or unimportant users is avoided, thereby better meeting a watching requirement of a specific user.

Figure 3:
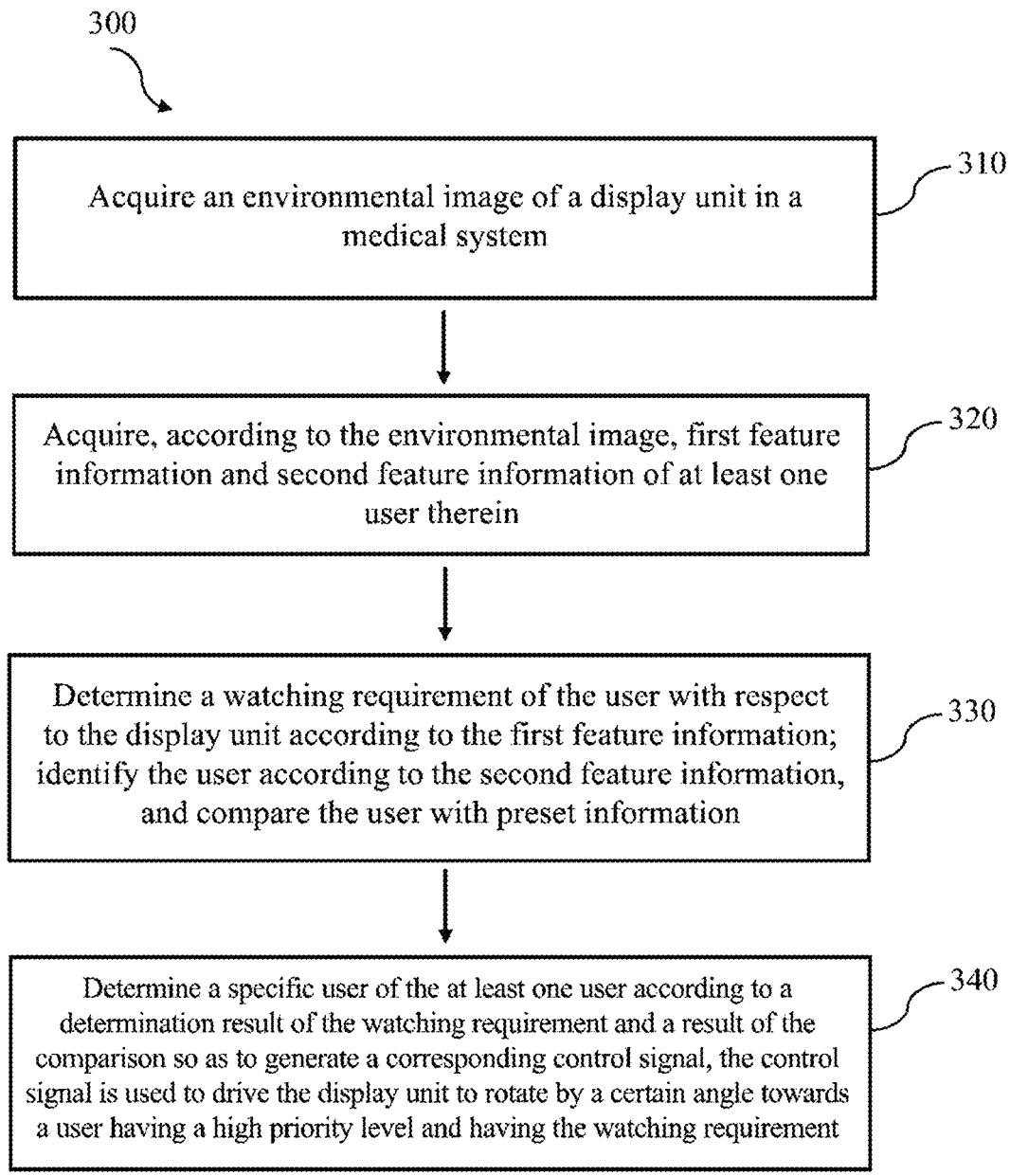
FIG. 3 shows a schematic diagram of a control signal generation method according to some other embodiments of the present invention.

In some embodiments, the above described feature information can be a combination of multiple types of feature information. For example, referring to FIG. 3, FIG. 3 shows a schematic diagram 300 of a control signal generation method according to some other embodiments of the present invention. After an environmental image of a display unit in a medical system is acquired in S310, step S320 can be performed, that is, first feature information and second feature information corresponding to the first feature information are acquired according to the environmental image. The above corresponds to the following meaning: the first feature information and the second feature information correspond to the same user. In this identification manner, a variety of information of the same user can be identified. For example, the first feature information can include eye information of the user, and the second feature information can include facial information corresponding to the eye information (namely the first feature information) of the user.

Correspondingly, a process of generating the control signal according to the above described feature information can be as step S330: determine a watching requirement of the user with respect to the display unit according to the first feature information; identify the user according to the second feature information, and compare the user with preset information. The watching requirement of the user with respect to the display unit can be determined according to the first feature information. When the first feature information includes the eye information, the determination can be performed by using eye capture technology in the prior art, or can be performed by using FIGS. 4a and 4b and some embodiments described in the following. In some embodiments, when it is determined that a direction of a line of sight of the user passes or substantially passes the above described display unit, it is determined that the user has a watching requirement.

In addition, the method can further include identifying the user according to the second feature information, and comparing the second feature information of the user with preset information. When the second information includes the facial information, for a presetting method of the preset information and a method for comparing the preset information with the user identified according to the second feature information, reference can be made to the embodiments described above, and details will not be described herein again. In some embodiments, the preset information can include priority information of different users. In this way, the priority level of the user identified in the environmental image can be determined by comparing the priority information of the user identified according to the second feature information.

In step S340, determine a watching requirement of the user with respect to the display unit according to the first feature information, and meanwhile determine a priority level of the user with reference to the second feature information corresponding to the first feature information, so as to generate a control signal. The above described control signal can be configured to: drive the display unit to rotate by a certain angle towards a specific user having a high priority level and having the watching requirement. The control signal can control a rotation angle by using a variety of methods or by using a method similar to that described above. For example, after the above described specific user is determined, a central point of the second feature information (such as a face contour of the specific user) is determined. Then, a connecting line between the central point and a central point of the display unit is determined. Further, an included angle formed by the connecting line and a perpendicular bisector of the display unit can be determined. The control signal can be configured according to the included angle, so as to cause the display unit to rotate in a direction to reduce or even eliminate the included angle. Configuration of the control signal can be varied. In some embodiments, a fixed rotation angle, such as 5° to 20°, can be preset. After rotation is performed once, the aforementioned steps are performed again to determine whether the above described included angle has been reduced to be less than a certain threshold. If so, rotation can be stopped; if not, a control signal can be transmitted again to control the display unit to rotate until the above described included angle is less than the threshold. In some embodiments, the above described certain angle can be consistent with the above described included angle. For example, when the measured included angle is 30°, a control signal of rotating by 30° is correspondingly transmitted to eliminate the included angle. In this way, the control signal is transmitted only once to achieve a function of allowing the specific user to watch easily. In certain scenarios, the specific user may be moving, and the environmental image can be acquired at certain time intervals, such as at an interval of 5-10 seconds, or at other time intervals, such that the specific user can watch easily in dynamic scenarios. It should be noted that the above described control signal is some preferred embodiments of the present invention, and other existing control methods are also applicable. In addition, the central point of the second feature information is not necessarily a strict central point of a plane or a body, and is allowed to deviate within a certain range. In some embodiments, a point in another position instead of the central point of the second feature information can also be selected.

The first feature information and the corresponding second feature information are identified, thereby more effectively improving efficiency of the user in watching the display unit or the medical system. Compared with the method in which only one type of feature information is utilized, combining two or more types of feature information can exclude a user having a high priority level but having no watching requirement, thereby preventing the display unit from erroneously determining a watching requirement. This has advantages in some application scenarios in which a large number of users are present.

Figure 4A:
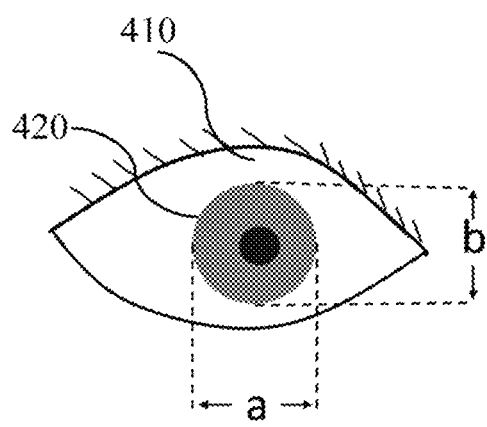
FIG. 4a shows a schematic diagram of an eye shape of a user watching a display unit according to some embodiments of the present invention.
Figure 4B:
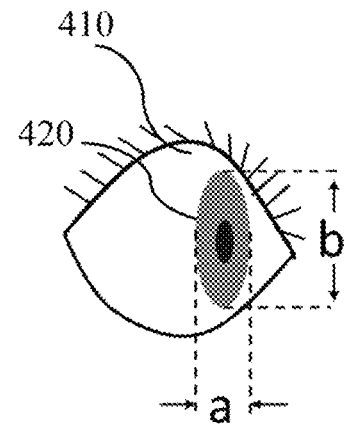
FIG. 4b shows a schematic diagram of an eye shape of a user not watching a display unit according to some embodiments of the present invention.

Referring to FIG. 4a and FIG. 4b, FIG. 4a shows a schematic diagram of an eye shape of a user watching a display unit according to some embodiments of the present invention; FIG. 4b shows a schematic diagram of an eye shape of a user not watching a display unit according to some embodiments of the present invention. An eye 410 of the user includes an iris 420. When the user watches the display unit, the iris 420 thereof is perpendicularly projected on the display unit. Correspondingly, when the acquired first feature information of the user in the above described method is eye information, an image of the iris 420 having a regular shape is acquired in the first feature information. In this case, a width a of the iris 420 in a horizontal direction is substantially equal to a height b in a vertical direction. When the user watches another position, the iris 420 is not perpendicularly projected on the display unit. Correspondingly, when the acquired first feature information of the user in the above described method is eye information, an image of the iris 420 having a regular shape cannot be acquired in the first feature information. Generally, a projection of the iris 420 will be oval, as shown in FIG. 4*b*. In this case, the width a of the iris 420 in the horizontal direction is obviously different from the height b in the vertical direction. A difference between the width a and the height b is determined. For example, a certain threshold is configured, and it is determined whether an absolute value of the difference between the width a and the height b is greater than the threshold. If so, it is determined that the user is not watching the display unit, and correspondingly this user has no watching requirement; if not, it is determined that the user is watching the display unit, and correspondingly this user has a watching requirement. It should be noted that the above described determination method of the watching requirement is merely one case of implementation of the present invention, and is not unique. Using an eyeball capture method in the prior art is also allowed. For example, it is determined whether a plane in which the iris is located is parallel to or substantially parallel to a plane in which the display unit is located; or, the above described medical system is trained in an application environment by using a machine learning method or the like, such that the medical system can identify an eye image of the user watching, in any specific position in the environment, the display unit. Details will not be described herein again.

Figure 5:
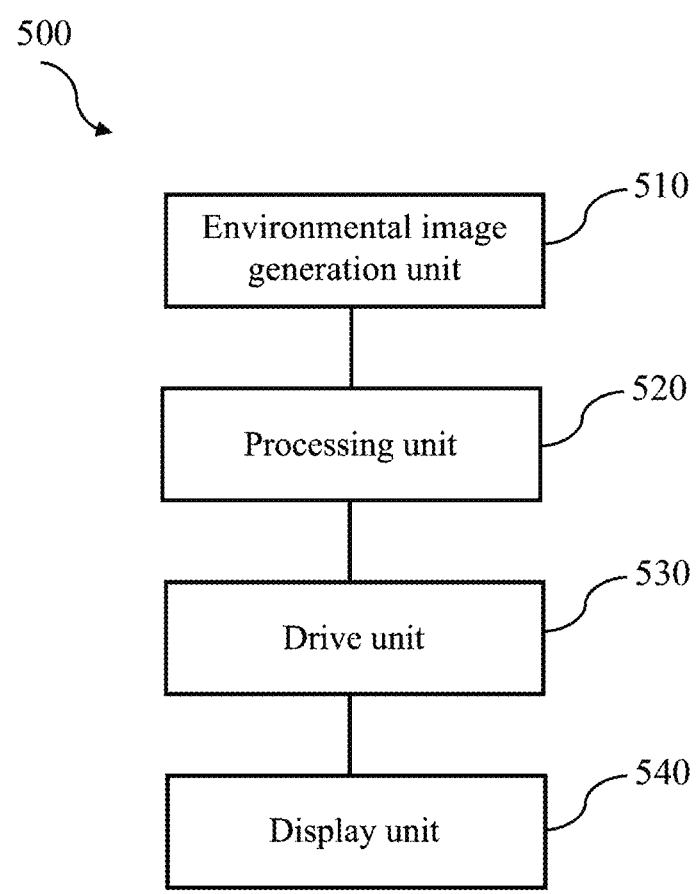
FIG. 5 shows a schematic structural diagram of a control apparatus of a display unit in a medical system according to some embodiments of the present invention.

Refer to FIG. 5. FIG. 5 shows a schematic structural diagram of a control apparatus 500 of a display unit in a medical system according to some embodiments of the present invention. The control apparatus 500 includes an environmental image generation unit 510, a processing unit 520, and a drive unit 530. The above described control apparatus 500 is connected to a display unit 540. The environmental image generation unit 510 can be used to generate an environmental image and transmit the environmental image to the processing unit 520; the processing unit 520 can be used to perform the method according to any one of the above described embodiments so as to transmit a control signal to the drive unit 530; the drive unit 530 is used to receive the control signal so as to drive the display unit 540 to rotate.

The environmental image generation unit 510 can be an imaging tool such as a camera, a video camera, and the like. The above described tool can be separately disposed independent of the display unit, and can also be integrated on the display unit. In certain cases, an imaging range covered by the imaging tool is limited. For example, image information at the back of the imaging tool cannot be acquired. In some embodiments of the present invention, multiple imaging tools are provided, and imaging ranges of the multiple imaging tools are appropriately arranged, such that the entire external environment can be covered to perform image acquisition. Images acquired by the environmental image generation unit 510 can be transmitted to the processing unit 520, such that the processing unit 520 can acquire the environmental image.

A medical system corresponding to the control apparatus 500 of the present invention is not limited to an ultrasound imaging system, a magnetic resonance imaging system, an X-ray imaging system, a monitoring system, an electrocardiogram system, an anaesthetic system, and the like. These medical systems generally have a processor used for imaging or monitoring. The processing unit 520 of the present invention can be independent of the above described processor, can be the above described processor, or can be part of the above described processor. The processor units 520 of the above described types are all regarded as part of the medical system of the present invention. After performing the method according to any one of the above described embodiments, the processor unit 520 generates a control signal, and transmits the control signal to the drive unit 530. In some embodiments, the above described medical system can include a monitoring system. When the above described control apparatus 500 is applied, important user information, such as a priority order of a chief physician, an associate chief physician, a head nurse, and a nurse, in a specific application scenario of the monitoring system can be pre-stored, and feature information (such as facial information) corresponding to the above described user can be stored. In some embodiments, the control apparatus 500 can select, according to the above described order, a user having a highest priority level, such as a chief physician, in the environmental image as a specific user so as to perform rotation. When no chief physician is present in the environmental image, sorting can be performed according to the above described priorities, and so on. Further, when identification of a variety of feature information, such as facial information and eye information, is further included, some users not watching a display unit of a patient monitor can be excluded according to the description in the above described embodiments. It should be noted that the description of the above described application scenario of the monitoring system is merely an example of the present invention, and is intended to facilitate understanding of the prominent technical effect of the present invention. None of the above described embodiments of the present invention is limited to a patient monitor, and the above described embodiments can be applied to any medical system.

The drive unit 530 has a mechanical structure of any type in the prior art, and this drive unit 530 is common in the art. Details will not be described herein again. It should be noted that the drive unit 530 can have a degree of freedom in any direction, such as a horizontal direction, a vertical direction, or a horizontal direction and a vertical direction. In addition, the method for driving the display unit 540 to rotate by a certain angle is introduced in some embodiments described above. The above described angle may not be horizontal or vertical, and in this case the driver 530 can achieve the effect of the above described rotation angle by means of a vector sum of an angle of horizontal motion and an angle of vertical motion. The present invention also does not limit a sequence of the above described horizontal motion and vertical motion, or the motion in the two directions can also be performed simultaneously.

A connection relationship between the display unit 540 and the drive unit 530 can be arbitrary. For example, the two can be integrally formed, or can be connected to each other detachably or in any other connection manner. A type of the display unit 540 can be dependent on a specific type of the medical system, or can be another type meeting the watching requirement of the user.

In some embodiments of the present invention, a non-transitory computer-readable storage medium can further be provided, the non-transitory computer-readable storage medium being used to store an instruction set and/or a computer program, wherein when executed by a computer, the instruction set and/or computer program causes the computer to perform the control method according to any one of the above described embodiments. The computer executing the instruction set and/or computer program can be a computer of the above described medical system, or can be other apparatuses/modules. In an embodiment, the instruction set and/or computer program can be programmed into a processor/controller of the computer.

The instructions described above may be combined into one instruction for execution, and any of the instructions may also be split into a plurality of instructions for execution. Moreover, the present invention is not limited to the instruction execution order described above. The term "computer" may include any processor-based or microprocessor-based system including a system that uses a microcontroller, a reduced instruction set computer (RISC), an application specific integrated circuit (ASIC), a logic circuit, and any other circuit or processor capable of executing the functions described herein. The above examples are merely exemplary and thus are not intended to limit the definition and/or meaning of the term "computer" in any way.

The instruction set may include various commands that instruct a computer acting as a processor or instruct a processor to perform particular operations, such as the methods and processes of various embodiments. The instruction set may be in the form of a software program, and the software program can form part of one or a plurality of tangible, non-transitory computer-readable media. The software may be in various forms such as system software or application software. In addition, the software may be in the form of a set of independent programs or modules, a program module within a larger program, or part of a program module. The software may also include modular programming in the form of object-oriented programming. The input data may be processed by the processor in response to an operator command, or in response to a previous processing result, or in response to a request made by another processor.

Some exemplary embodiments have been described above; however, it should be understood that various modifications may be made. For example, if the described techniques are performed in a different order and/or if the components of the described system, architecture, device, or circuit are combined in other manners and/or replaced or supplemented with additional components or equivalents thereof, a suitable result can be achieved. Accordingly, other implementation manners also fall within the protection scope of the claims.

The invention claimed is:

1. A method of controlling a display of a medical system, the method comprising:
   acquiring an environmental image of an area surrounding the display;
   acquiring, according to the environmental image, feature information of a plurality of users shown in the environmental image;
   determining a specific user of the plurality of users according to the feature information to generate a control signal, the determining the specific user comprising:
      obtaining first feature information and second feature information corresponding to the specific user from the feature information;
      determining a watching requirement of the specific user based on the first feature information;
      comparing the second feature information and preset information; and
      determining the specific user of the plurality of users according to the comparison and watching requirement; and
   generating a control signal for driving the display to rotate based on third feature information of the specific user.

2. The method according to claim 1, wherein the feature information comprises facial information or eye information of the user.

3. The method according to claim 1, wherein the control signal comprises a signal for driving the display unit to rotate by a certain angle.

4. The method according to claim 1, wherein the preset information comprises priority information of different users, and
   comparing the identified user with preset information comprises:
      comparing the identified user with the priority information, and
      determining a priority level of the user.

5. The method according to claim 4, wherein the control signal is configured to:
   drive the display unit to rotate by a certain angle towards the specific user having a high priority level.

6. The method according to claim 1, wherein the first feature information comprises the eye information of the user; the second feature information comprises the facial information of the user.

7. The method according to claim 1, wherein the preset information comprises priority information of different users;
   comparing the user with preset information further comprises:
      comparing the user with the priority information, and
      determining a priority level of the user.

8. The method according to claim 7, wherein the control signal is configured to:
   drive the display unit to rotate by a certain angle towards the specific user having a high priority level and having the watching requirement.

9. A control apparatus of a display unit in a medical system, the control apparatus comprising:
   an environmental image generation unit;
   a processing unit; and
   a drive unit,
   wherein the environmental image generation unit is used to generate an environmental image and transmit the environmental image to the processing unit; the processing unit is used to perform the method according to claim 1 so as to transmit a control signal to the drive unit; and
   the drive unit is used to receive the control signal so as to drive the display unit to rotate.

10. A medical system, comprising the control apparatus according to claim 9.

11. A non-transitory computer-readable storage medium for storing a computer program, wherein when executed by a computer, the computer program causes the computer to perform the control method according to claim 1.

12. The method according to claim 1, wherein generating the control signal comprises:
   identifying a central point on the specific user;
   determining a connecting line between the central point on the user and a central point on the display; and determining a display rotation which reduces an angle between the connecting line an a perpendicular bisector of the display.

\* \* \* \* \*